United States Patent [19]

Perrin et al.

[11] 4,246,670
[45] Jan. 27, 1981

[54] PROCESS FOR IMPROVING THE COLOR YIELD AND FASTNESS PROPERTIES OF DYEINGS PRODUCED WITH ANIONIC DYES ON CELLULOSE FIBRE MATERIAL AND CATIONIC FIBRE-REACTIVE COMPOUNDS

[75] Inventors: Pierre Perrin, Basel; Gert Hegar, Schönenbuch; Gérald Siegrist; Herbert Seiler, both of Riehen; Ulrich Horn, Basel, all of Switzerland

[73] Assignee: Ciba-Geigy Corporation, Ardsley, N.Y.

[21] Appl. No.: 58,045

[22] Filed: Jul. 16, 1979

Related U.S. Application Data

[62] Division of Ser. No. 805,208, Jun. 9, 1977, Pat. No. 4,180,664.

[30] Foreign Application Priority Data

Jun. 16, 1976 [CH] Switzerland ............... 7674/76

[51] Int. Cl.³ ............... D06M 13/46; D06P 3/60; D06P 1/66; C07D 251/50
[52] U.S. Cl. ............... 8/566; 8/190
[58] Field of Search ............... 8/188, 190, 566

[56] References Cited

U.S. PATENT DOCUMENTS 3,347,617  10/1967  Ulrich et al. ............... 8/188

FOREIGN PATENT DOCUMENTS 1094699  12/1960  Fed. Rep. of Germany.

OTHER PUBLICATIONS

Derwent Abs. 14644/64, "Treatment of Cellulosic Fiber", (J39-14644) Jul. 24, 1964, Sumitomo Kagaku Kogyo Co.
Derwent Abs. 1085492, "Improved Handling", DT 1085492, Jul. 21, 1960, Chem. Fab. Grunau.
Derwent Abs. 92065/05, "Triazine Colouring Assistant for Cellulose Dyeing", IA7104349 DAIT 2-3-71.

*Primary Examiner*—Joseph L. Schofer
*Assistant Examiner*—Herbert J. Lilling
*Attorney, Agent, or Firm*—Edward McC. Roberts

[57] ABSTRACT

A process for improving the color yield and the wetfastness properties of dyeings produced on cellulose fibre material with anionic dyes, which process comprises treating the cellulose material before, during or after dyeing, with a cationic fibre-reactive compound of the formula

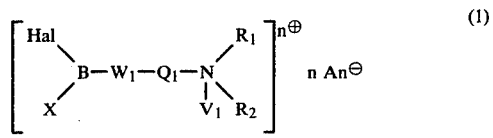

wherein
B represents a mono- or polynuclear heterocyclic radical,
Hal represents a reactive halogen atom,
X represents halogen, lower alkoxy, lower alkylthio, phenoxy, phenylthio, $-NH_2$,

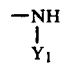

or the group of the formula

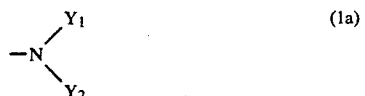

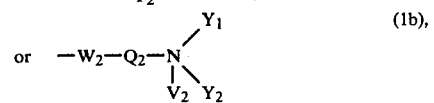

each of $W_1$ and $W_2$ independently represents the direct bond,

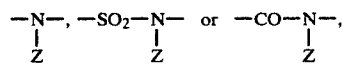

Z represents hydrogen, lower alkyl or hydroxy-lower alkyl,
each of $Q_1$ and $Q_2$ independently represents an aliphatic or cycloaliphatic radical,
each of $R_1$, $R_2$, $V_1$, $V_2$, $Y_1$ and $Y_2$ independently represents lower alkyl, or lower alkyl or benzyl each of which is substituted by halogen, hydroxy or cyano, or
each of the pair of substituents $R_1$ and $R_2$ and $Y_1$ and $Y_2$ together with the nitrogen atom to which it is attached independently represents a 5- or 6-membered heterocyclic ring, or
each of $R_1$, $R_2$ and $V_1$ and $Y_1$, $Y_2$ and $V_2$ together with the nitrogen atom to which it is attached independently represents a pyridine ring, or, if $W_1$ and $W_2$ are

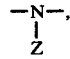

each of Z and $V_1$ and Z and $V_2$ together with the group $>N-Q_1-N<$ or $>N-Q_2-N<$ independently also represents a divalent heterocyclic radical,
An⁻ represents the anion of an organic or inorganic acid, and n is 1 or 2,
with the proviso that an optional aftertreatment of the cellulose material is carried out according to a padding process.

17 Claims, No Drawings

PROCESS FOR IMPROVING THE COLOR YIELD AND FASTNESS PROPERTIES OF DYEINGS PRODUCED WITH ANIONIC DYES ON CELLULOSE FIBRE MATERIAL AND CATIONIC FIBRE-REACTIVE COMPOUNDS

This is a divisional of application Ser. No. 805,208 filed on June 9, 1977 now U.S. Pat. No. 4,180,664.

The present invention relates to a process for improving the colour yield and fastness properties of dyeing produced with anionic dyes on cellulose fibre material, to the liquors used for carrying out this process, which contain cationic fibre-reactive compounds as fixing agent, to the fibrous material treated in accordance with this process, and also to the novel cationic fibre-reactive compounds themselves and to a process for their manufacture.

It is known to dye cellulose material with anionic substantive or reactive dyes from aqueous medium without the addition of fixing agents. However, in many cases the colour yield of the dyeings and, in particular when substantive dyes are used, the wetfastness properties are unsatisfactory. Although there are fixing agents by means of which these drawbacks can be diminished, the results nonetheless still leave something to be desired.

It is known, for example, that polyalkylenepolyamines can be used as fixing agents for substantive or reactive dyes. However, these compounds result in a marked impairment of the lightfastness. The proposal has furthermore been made to use fixing agents containing an epoxy group for improving the wetfastness properties of dyeings produced with substantive dyes on cellulose material. However, these fixing agents react sluggishly, so that the fixation has to be carried out under fairly drastic conditions, for example at elevated temperature or high pH values or with a lengthy reaction time.

The present invention provides cationic compounds which can be used as fixing agents for amionic dyes and which, surprisingly, effect a marked improvement in the colour yield both of dyeings on cellulose material with reactive and substantive dyes, while in addition the wetfastness properties, especially with substantive dyes, are substantially improved and the lightfastness is not impaired.

On account of their pronounced reactivity, the compounds of the present invention can be applied under particularly mild conditions, so that the process can be carried out often at lower temperatures and/or lower pH values or also with shorter reaction times than when using the fixing agents referred to above which contain an epoxy group as reactive radical.

Accordingly, the present invention provides a process for improving the colour yield and the wetfastness properties of dyeings produced with anionic dyes on cellulose fibre material, which process comprises treating the cellulose material before, during or after dyeing with a cationic fibre-reactive compound of the formula

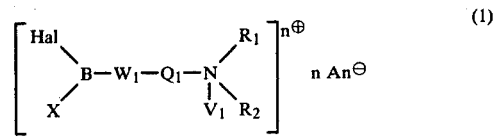

wherein
B represents a mono- or polynuclear heterocyclic radical,
Hal represents a reactive halogen atom,
X represents halogen, lower alkoxy, lower alkylthio, phenoxy, phenylthio, $-NH_2$,

or the group of the formula

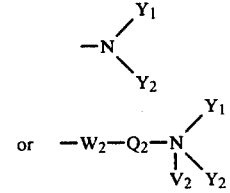

each of $W_1$ and $W_2$ independently represents the direct bond,

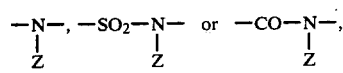

Z represents hydrogen, lower alkyl or hydroxy-lower alkyl, each of
$Q_1$ and $Q_2$ independently represents an aliphatic or cycloaliphatic radical,
each of $R_1$, $R_2$, $V_1$, $V_2$, $Y_1$ and $Y_2$ independently represents lower alkyl or lower alkyl or benzyl each of which is substituted by halogen, hydroxyl or cyano, or
each of the pair of substituents $R_1$ and $R_2$ and $Y_1$ and $Y_2$ together with the nitrogen atom to which it is attached represents a 5- or 6-membered, preferably saturated, heterocyclic ring or
each of $R_1$, $R_2$ and $V_1$ and $Y_1$, $Y_2$ and $V_2$ together with the nitrogen atom to which it is attached represents a pyridine ring, or, if $W_1$ and $W_2$ are

each of Z and $V_1$ and Z and $V_2$ together with the group $>N-Q_1-N<$ or $>N-Q_2-N<$ also represents a divalent heterocyclic radical, in particular an imidazolidino or piperazino ring,
$An^\ominus$ represents the anion of an organic or inorganic acid, and n is 1 or 2,
with the proviso that an optional aftertreatment is carried out by the padding process.

In the definition of the radicals of the cationic fibre-reactive compounds, lower alkyl and lower alkoxy as a rule denote those groups or group components which contain 1 to 4, especially 1 to 3, carbon atoms, for example methyl, ethyl, n-propyl, isopropyl, or n-butyl, and methoxy, ethoxy or isopropoxy. Halogen in connection with all substituents referred to throughout this specification denotes, for example, bromine, fluorine or preferably chlorine.

The heterocyclic radical B is in particular a nitrogen-containing heterocyclic ring which optionally contains a fused benzene ring and/or is substituted by further halogen atoms. Preferably B represents a pyrimidine or triazine ring. The pyrimidine ring B advantageously contains a further halogen atom. Examples of such a heterocyclic ring B are the 1,3,5-triazine, pyrimidine, 5-chloropyrimidine, quinoxaline, quinazoline or phthalazine ring.

X represents in particular lower alkoxy, —$NH_2$ or the group of the formula (1b). Lower alkoxy represented by X is preferably methoxy, ethoxy or isopropoxy, and lower alkylthio represented by X is preferably methylthio or ethylthio.

Hal represents for example bromine and preferably chlorine or fluorine.

Each of $W_1$ and $W_2$ represents in particular the group

and Z is preferably hydrogen.

An aliphatic radical represented by each of $Q_1$ and $Q_2$ is in particular an alkylene group which contains 2 to 4 carbon atoms and can be straight-chain or branched. A cycloaliphatic radical is in particular the cyclohexylene group. Preferably, $Q_1$ and $Q_2$ represent ethylene or in particular propylene.

The radicals R and Y can be different from each other or they are preferably identical. $V_1$ and $V_2$ are also preferably the same.

Lower alkyl radicals represented by R, Y and V are in particular methyl or ethyl radicals. Substituted lower alkyl radicals R, Y and V are in particular haloalkyl, cyanoalkyl and hydroxyalkyl, each containing 2 to 4 carbon atoms, for example 2-chloroethyl, 2-cyanoethyl, 2-hydroxyethyl and 3-hydroxypropyl. Preferred radicals R, Y and V are methyl and ethyl. The radicals V can also preferably be benzyl.

A heterocyclic radical represented by each of the pair of substituents $Y_1$ and $Y_2$ and $X_1$ and $X_2$ together with the nitrogen atom to which it is attached is, for example, a pyrrolidino, piperidino, pipecolino or morpholino radical.

Possible anions $An^\ominus$ are both anions of inorganic acids, for example the chloride, bromide, fluoride, sulphate or phosphate ion, and of organic acids, for example of aromatic or aliphatic sulphonic acids, such as the benzenesulphonate, p-toluenesulphonate, methanesulphonate or ethanesulphonate ion, and also the anions of acid alkyl esters of inorganic acids, such as the methosulphate and ethosulphate ion. $An^\ominus$ is in particular the chloride, bromide or methosulphate ion.

Important cationic compounds of the formula (1) have the formula

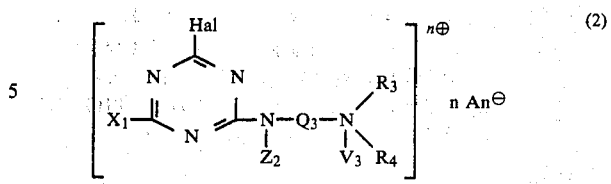

wherein
$X_1$ represents lower alkoxy, —$NH_2$ or the group of the formula

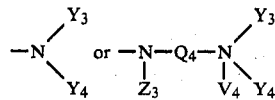

each of $Q_3$ and $Q_4$ independently represents alkylene of 2 to 4 carbon atoms,
each of $Z_2$ and $Z_3$ independently represents hydrogen, methyl or ethyl,
each of $R_3$, $R_4$, $Y_3$ and $Y_4$ represents lower alkyl, each of $V_3$ and $V_4$ represents lower alkyl or benzyl and Hal, n and $An^\ominus$ have the given meanings.

Particularly interesting triazine compounds are those of the formula

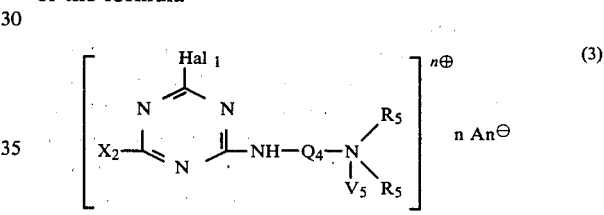

wherein
$Hal_1$ represents fluorine or chlorine,
$X_2$ represents lower alkoxy, —$NH_2$ or the group of the formula

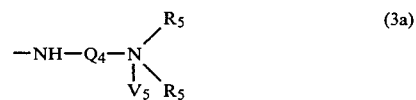

$Q_4$ represents ethylene or propylene,
$R_5$ represents methyl or ethyl,
$V_5$ represents methyl, ethyl or benzyl, and
$An^\ominus$ and n have the given meanings.

Preferred triazine compounds of the formula (3) are those in which $X_2$ represents lower alkoxy and $Hal_1$ represents chlorine.

The cationic compounds of the formula (1) are manufactured in a manner which is known per se, preferably by reacting a compound of the formula

wherein
B, X and Hal have the given meanings,
T represents the direct bond, —$SO_2$— or —CO—, and D represents halogen,
with a quaternary ammonium salt of the formula

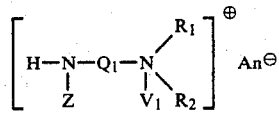 (5)

wherein $An^{\ominus}$, Z, $Q_1$, $R_1$, $R_2$ and $V_1$ have the given meanings. For example the cationic compounds can be obtained by reaction of cyanuric chloride or monochlorotrifluoropyrimidine with the corresponding amines.

The reaction conditions for the manufacture of the compounds of the formula (1) are to be so chosen that no premature exchange of mobile substituents takes place either as a consequence of too high a pH value of the reaction medium or of too high a temperature. The process is therefore carried out preferably in a strongly dilute aqueous medium under as mild temperature and pH conditions as possible, advantageously at temperatures between 0° and 50° C. and pH values between 6 and 8, preferably in the presence of agents which neutralise mineral acid, for example sodium carbonate or sodium hydroxide.

The treatment of the cellulose material with the cationic compound of the formula (1) is effected preferably by a padding process, in which the material is first impregnated with the fixing agent, for example by slop-padding or printing, and then subjected to a fixing process. This application can be carried out before, during or after the dyeing. It is preferred to carry out the treatment before or during the dyeing. Suitable padding processes are those which are suitable for the application of reactive dyes, for example the thermofixing, single bath slop-pad steaming, pad-jig, pad-dry, pad-roll and pad-steam process, with or without first drying the goods, and also the pressure-steam process. Preferably the treatment is carried out by the cold pad-batch process and in particular during the dyeing.

The impregnating can be carried out at 20° to 50° C., but preferably at room temperature. The fixation process is effected for example by steaming at 100°—105° C. or by a dry treatment at 120° to 220° C. In a fixation process by the cold pad-batch process, the padded material is stored for 4 to 48 hours, preferably for 6 to 12 hours, at room temperature.

The treatment of the cellulose material can also be effected before or during the dyeing by the exhaustion process. In this case it is possible to carry out the process at temperatures in the range between 20° and 100° C.

The liquor ratio can be chosen within a wide range, for example from 1:4 to 1:100, preferably from 1:10 to 1:50.

The treatment liquors contain the compound of the formula (1) preferably in an amount between 0.1 and 20% by weight, in particular between 0.5 and 10% by weight, referred to the weight of the cellulose material, or, in padding liquors, of 1 to 100 g/l, preferably 10 to 50 g/l, of padding liquor, whilst the squeezing effect in the padding process is advantageously 60 to 90% by weight.

In addition to the cationic reactive compound of the formula (1), these liquors also contain alkali, for example sodium carbonate, sodium bicarbonate, sodium hydroxide or alkali donors, for example sodium trichloroacetate, and also, if appropriate, further additives, such as urea, thickeners, for example alginates, or polyacrylates, or salts, for example sodium chloride, or wetting agents.

The pretreatment with the compounds of the formula (1) can advantageously be combined with other pretreatment operations. For example, the reactive fixing agent of the formula (1) can be added to the alkaline bath in which raw cotton is customarily boiled before dyeing in order to remove impurities and thus the purification and pretreatment with the fixing agent can be carried out in one step.

When simultaneously applying reactive compound of the formula (1) and dye, it must be taken into account that the solubility of the dyes can in some cases be reduced through the presence of the compounds of the formula (1). This effect is also dependent on the nature of the alkali simultaneously used. In general, the solubility is reduced less when adding sodium hydroxide than when adding sodium carbonate.

Suitable cellulose material can be that from natural and regenerated cellulose, for example hemp, linen, jute, viscose rayon, viscose staple fibre, and in particular cotton and also fibre blends, for example those of polyester/cotton, in which the polyester portion is optionally dyed before or afterwards.

The material to be dyed can be in any desired states of processing, for example as loose material (flocks), as doubled, prestretched staple fibre ribbon or in the form of filaments, yarns, wovens or knits.

By reactive dyes are meant the conventional anionic dyes which form a chemical bond with cellulose, for example the "Reactive Dyes" listed in the Colour Index, 3rd Edition (1971), Vol. 3, on pp. 3391–3562.

Suitable substantive dyes are the conventional anionic direct dyes, for example the "Direct Dyes" listed in the above Colour Index, Vol. 2, on pp. 2005–2478.

The present invention also relates to the aqueous liquors used for carrying out the process described herein. These liquors contain a compound of the formula (1) and optionally alkali or alkali donors and the further additives mentioned above.

In the following illustrative, but non-limitative, Examples, the percentages are by weight unless otherwise stated. The amounts of dye refer to commercially available, i.e. extended, products, and of fixing agents to pure substance. The Colour Index numbers refer to the 3rd Edition of the Colour Index.

EXAMPLE 1

40 g of a fixing agent of the formula

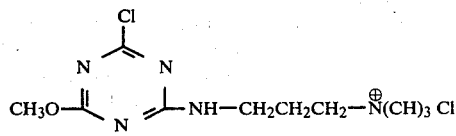 (11)

are dissolved at room temperature in a mixture of 185 ml of water and 15 ml of 30% sodium hydroxide solution. To this solution is added a solution of a blue direct dye C.I. 24 401 in 800 ml of water. A bleached mercerised cotton fabric is slop padded with this solution on a padder, squeezed out to a pick-up of 75% by weight, rolled up, wrapped in a plastic sheet and left to stand for 6 hours at room temperature. The fabric is then rinsed first in cold and then twice in boiling water for 10–15 minutes, and dried. A level, deep, bluish-green dyeing of good wash- and lightfastness is obtained.

By using equal amounts of 2-epoxypropyl-trimethylammonium chloride or N-(2-epoxypropyl)-N-methyl-morpholinium chloride instead of the fixing agent of the formula (11) and carrying out the procedure described above, at least twice as long a storage time is required to obtain the same depths of shade.

An equally good result is obtained by using an equal amount of the compound of the formula

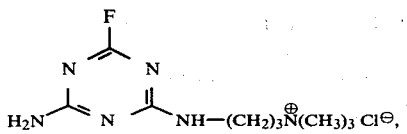
(12)

instead of the fixing agent of the formula (11).

EXAMPLE 2

20 g of a fixing agent of the formula

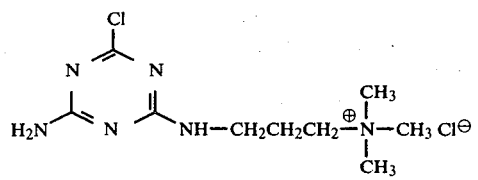
(13)

are dissolved at room temperature in a mixture of 485 ml of water and 15 ml of 30% sodium hydroxide solution. To this solution is added a solution of 20 g of the red dye of the formula

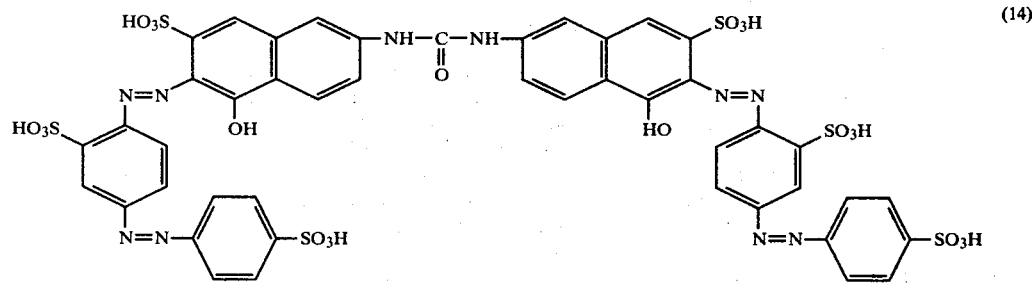
(14)

in 500 ml of water. A bleached mercerised cotton fabric is slop padded with this solution on a padded, squeezed out to a pick-up of 75% by weight, rolled up, wrapped in a plastic sheet and left to stand for 24 hours at room temperature. The fabric is then rinsed first in cold and then twice in boiling water for 10 to 15 minutes, and dried. A red dyeing of good wash- and light-fastness is obtained.

A substantially lighter dyeing is obtained by using the same amount of the dichlorotriazine compound described in DAS No. 1,094,699, Example 1, instead of the fixing agent of the formula (13).

EXAMPLE 3

A cotton fabric is slop padded on a padder at room temperature with an aqueous liquor which contains, per liter, 20 g of sodium carbonate and 20 g of a reactive fixing agent of the formula

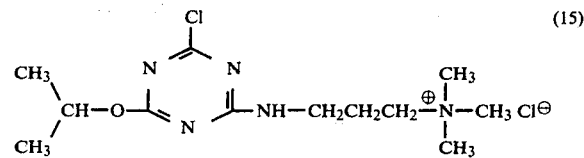
(15)

and squeezed out to a liquor pick-up of 80% by weight. The fabric is then dried for 2 minutes at 120° C. and washed cold.

The pretreated cotton fabric is then slop padded with an aqueous liquor which contains, per liter, 50 g of urea and 20 g of the direct dye C.I. 29 025, then rolled up, wrapped in a plastic sheet and stored for 20 hours at room temperature. The fabric is then rinsed at 80° C. A yellow dyeing of good wetfastness properties is obtained, which is deeper than that obtained on fabric which has not been pretreated.

An equally good result is obtained by using an equal amount of the compound of the formula (12) instead of the fixing agent of the formula (15).

EXAMPLE 4

A bleached mercerised cotton cretonne fabric is slop padded at room temperature on a padder with an aqueous solution which contains, per liter, 40 g of a reactive fixing agent of the formula (16)

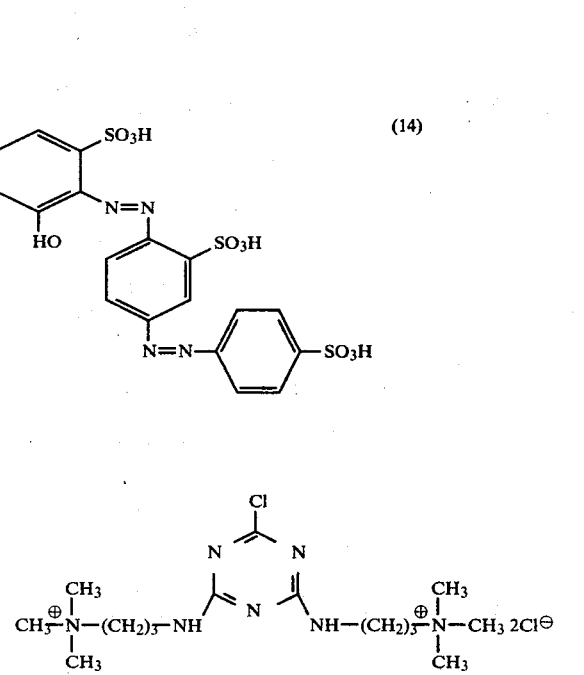

30 ml of 30% sodium hydroxide solution. The fabric is squeezed out to a pick-up of 90%, rolled up, wrapped in a plastic sheet and stored for 24 hours at room temperature. It is then rinsed cold and dried.

The pretreated goods are then slop padded with an aqueous liquor which contains, per liter, 50 g of urea, 20 g of sodium carbonate and 15 g of the reactive dye of the formula

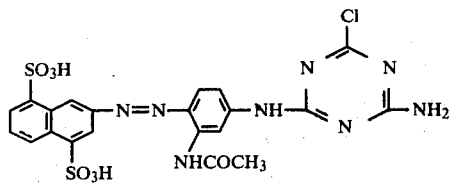
(17)

then, without first being dried, steamed with saturated steam for 30 seconds, rinsed and soaped at the boil. The fabric is dyed yellow and compared with fabric which has not been pretreated and has been dyed in the same way, has a substantially deeper shade of good wet- and lightfastness.

EXAMPLE 5

A bleached cotton fabric is padded on a padder to a pick-up of 70% with an aqueous liquor which contains per liter 20 g of a direct dye C.I. 27 925

15 ml of 30% sodium hydroxide solution, and 40 g of a fixing agent of the formula (16).

The fabric is then dried at 100° C., thermofixed for 5 minutes at 150° C., washed firstly with cold water and then rinsed twice at the boil. A deep blue dyeing is obtained.

A much weaker dyeing is obtained if the compound described in Example 2, lines 53–86, of German patent 633 691 is used instead of the fixing agent of the formula (16).

EXAMPLE 6

10 g of a cotton fabric which has been dyed or printed in the conventional manner with the direct dye C.I. 24 401 in reference type strength is slop-padded on a padder to a liquor pick-up of 75% by weight with an aqueous liquor which contains, per liter, 40 g of a fixing agent of the formula (11) and 15 ml of 30% sodium hydroxide solution. The fabric is then rolled up, wrapped in a plastic sheet and stored at room temperature for 6 hours. The pretreated fabric is then rinsed cold, soaped at the boil, rinsed again and dried. The cotton fabric is dyed a deep blue shade of very good wetfastness properties.

The bulk of the dye becomes detached when fabric which has not been subjected to an aftertreatment with fixing agent is soaped at the boil. The wetfastness properties of such fabric are also substantially poorer.

EXAMPLE 7

A blended fabric consisting of 67% by weight of polyester and 33% by weight of cotton is slop-padded on a two-roll padder with a liquor which contains, per liter.

3.6 g of a disperse dye of the formula

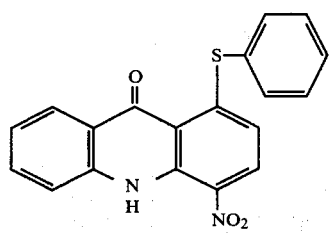
(18)

0.66 g of a direct dye C.I. 29 025

2 of sodium alginate, and 0.5 ml of 80% acetic acid, squeezed out to a liquor pick-up of 75% by weight, dried at 100° C., and thermofixed for 60 seconds at 210° C.

Thereafter the fabric is slop-padded with a liquor which contains, per liter, 40 g of a fixing agent of the formula (11) and 15 ml of 30% sodium hydroxide solution and steamed for 45 seconds with saturated steam of 100°–102° C.

The fabric is then rinsed continuously cold and at the boil.

A bolden yellow fabric with very good wetfastness properties, especially good washfastness at 60° C., is obtained.

An equally good result is obtained by using the same amount of the fixing agent of the formula (15) instead of the fixing agent of the formula (11).

Instead of by steaming, the fixation of the direct dye can also be accomplished by rolling up the fabric padded with the fixing agent and wrapping it in a plastic sheet and storing it for 6 hours at room temperature. The fabric is subsequently washed off as described above.

EXAMPLE 8

Viscose staple fibre cretonne is padded on a two-roll padder at 20° C. with an aqueous liquor which contains per liter 15 g of a direct dye C.I. 24 401, 15 ml of 30% sodium hydroxide solution, and 30 g of a fixing agent of the formula (13).

The fabric is squeezed out to a liquor pick-up of 90% by weight and subsequently steamed for 5 minutes with saturated steam of 100° to 102° C. The dyeing is then rinsed continuously cold and at 80° C. The fabric is dyed a strong red shade of good wetfastness properties.

EXAMPLE 9

30 g of a fixing agent of the formula (13) are dissolved at room temperature in a mixture of 470 ml of water and 30 ml of 30% sodium hydroxide solution. To this solution is added a solution of 30 g of a turquoise blue reactive dye C.I. 74 460 in 500 ml of water. A bleached mercerised cotton fabric is padded with this solution on a padder, squeezed out to a pick-up of 75%, rolled up, wrapped in a plastic sheet and allowed to stand for 24 hours at room temperature. The fabric is then rinsed firstly in cold and then in boiling water for 10 to 15 minutes, and dried. The fabric is dyed in a level, deep turquoise blue shade of good wash- and lightfastness.

A markedly weaker dyeing is obtained by dyeing as described above but without the addition of the fixing agent of the formula (13) to the padding liquor.

EXAMPLE 10

A cotton fabric which has been dyed or printed in conventional manner in reference type strength with the dye of the formula

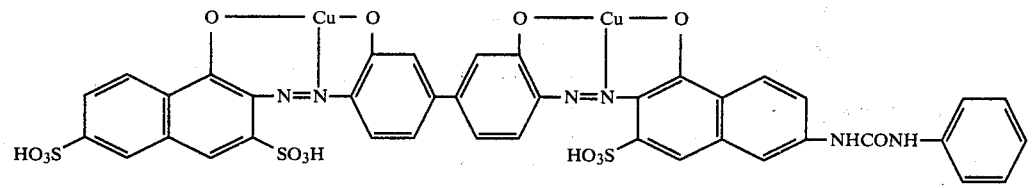

is padded on a padder with an aqueous liquor which contains, per liter, 30 g of a fixing agent of the formula (11) and 20 g of sodium carbonate. The fabric is squeezed out to a pick-up of 75% and subsequently dried for 2 minutes at 120° C.

The aftertreated dyeing is continuously rinsed cold and hot, and dried. A deep blue dyeing of good wetfastness properties is obtained.

EXAMPLE 11

20 g of a fixing agent of the formula (15) are dissolved at room temperature in a mixture of 485 ml of water and 15 ml of 30% sodium hydroxide solution. To this solution is added a solution of 20 g of the scarlet dye of the formula

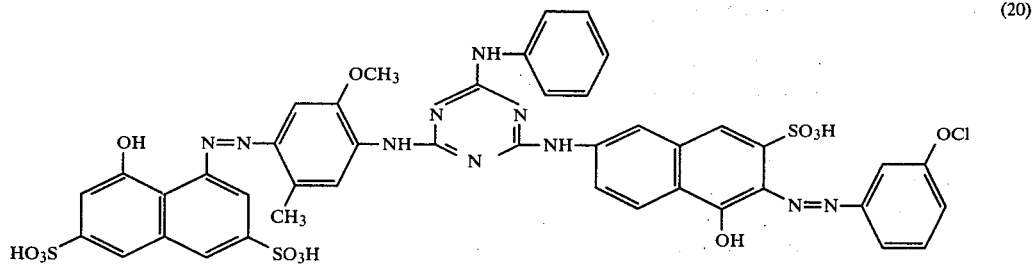

in 500 ml of water. A bleached mercerised cotton fabric is padded with this solution on a padder, squeezed out to a pick-up of 75%, rolled up, wrapped in a plastic sheet and allowed to stand for 6 hours at room temperature. The fabric is rinsed firstly in cold and then twice in boiling water for 10 to 15 minutes, and dried. A level, deep scarlet dyeing of good wash- and lightfastness is obtained.

EXAMPLE 12

The fixing agent of the formula (11) can be prepared as follows:

A solution of 41.6 g of trimethyl-(3-aminopropyl)-ammonium chloride in 50 ml of water is added dropwise at 5° C. to a solution of 54 g of 2-methoxy-4,6-dichloro-1,3,5-triazine in 50 ml of water, while keeping the pH value of the solution between 7 and 8 by the addition of 30% sodium hydroxide solution. The reaction mixture is then diluted with 4000 ml of acetone and the precipitate which forms is collected by filtration, giving 18 g of a white compound of the formula (11) with a melting point of 250° C.

EXAMPLE 13

The fixing agent of the formula (13) can be prepared as follows:

33 g of 2-amino-4,6-dichloro-1,3,5-triazine are dissolved at 40° C. in 50 ml of water. To this solution is slowly added dropwise a 21% aqueous solution of 30.8 g of N,N,N-trimethylpropylene-diammonium dichloride, while keeping the pH value of the reaction mixture constant at 7 with sodium hydroxide solution. The reaction mixture is then concentrated in vacuo and the residue is extracted with ethanol. The ethanol is then removed to give 59 g of a solid compound of the formula (13).

EXAMPLE 14

The fixing agent of the formula (15) can be prepared as follows:

12.5 g of 2,4-dichloro-6-isopropoxy-1,3,5-triazine are suspended at 2° C. in 50 ml of water. To this suspension is then added dropwise a solution of 9.2 g of trimethyl-(3-aminopropyl)-ammonium chloride in 30 ml of water over the course of 5 hours, while keeping the pH of the suspension at 7.5 with a 30% sodium hydroxide solution. The reaction mixture is concentrated and the residue extracted with methanol. The methanol is distilled off in vacuo and the residue washed with 200 ml of diethyl ether, affording 18 g of the fixing agent of the formula (15).

EXAMPLE 15

The fixing agent of the formula (16) is prepared in the following way:

42 g of cyanuric chloride are suspended in a 300 g ice-water mixture. To this suspension is added, with stirring, a solution of 30.5 g of trimethyl-(3-aminopropyl)-ammonium chloride in 200 ml of water, while keeping the pH value of the reaction mixture at 8 by the addition of 30% sodium hydroxide solution. After 2 hours the temperature is raised to 25° C. and a solution of 30.5 g of trimethyl-(3-aminopropyl)-ammonium chloride in 200 ml of water is again added dropwise. The temperature is thereafter raised to 40° C. and stirring is continued. The reaction mixture is then concentrated, whereupon the residue is extracted with methanol. The methanol is distilled off in vacuo, affording 108 g of the compound of the formula (16) as a white residue.

EXAMPLE 16

The fixing agent of the formula (12) can be prepared as follows:

90 g of a 21% solution of N,N,N-trimethylpropylene-diammonium dichloride are diluted with 300 g of water and adjusted to pH 7 by the addition of 2 N sodium hydroxide solution. To this solution is added at room temperature a solution of 13.5 g 2-amino-4,6-difluoro-1,3,5-triazine in 50 g of acetone. The pH of the solution is kept at 7 to 7.5 by the simultaneous addition of 2 N sodium hydroxide solution. When the condensation is complete, the reaction mixture is concentrated under reduced pressure and the residue is extracted with ethanol. The alcohol is then removed to give 25 g of a solid compound of the formula (12), which is readily soluble in water.

What we claim is:

1. A process for improving the color yield and the wetfastness properties of dyeings produced with anionic dyes on cellulose fibers, which process comprises treating said fibers before, during or after dyeing with a cationic fiber-reactive compound of the formula

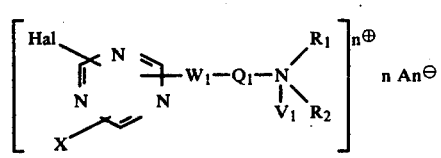

wherein

Hal is a reactive halogen atom,

X is halogen, lower alkoxy, lower alklthio, phenoxy, phenylthio, —NH$_2$, —NH(Y$_1$) or a group of the formula

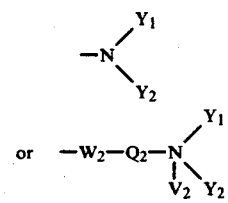

each of W$_1$ and W$_2$ independently is the direct bond, —N(Z)—, —SO$_2$—N(Z)— or —CON(Z)—, Z is hydrogen, lower alkyl or hydroxy-lower alkyl, each of Q$_1$ and Q$_2$ independently is an aliphatic or cycloaliphatic radical, selected from the group consisting of alkylene of 2 to 4 carbon atoms and cyclohexylene, each of R$_1$, R$_2$, V$_1$, V$_2$, Y$_1$ and Y$_2$ independently is lower alkyl or benzyl or lower alkyl or benzyl each of which is substituted by halogen, hydroxyl or cyano, An$^\ominus$ is the anion of an organic acid, and n is 1 or 2.

2. A process according to claim 1 which comprises the use of a compound of the formula (1) wherein X represents lower alkoxy, —NH$_2$ or the group of the formula (1b).

3. A process according to claim 1 which comprises the use of a compound of the formula (1) wherein each of W$_1$ and W$_2$ independently represents

4. A process according to claim 4 wherein Z represents hydrogen.

5. A process according to claim 1 which comprises the use of a compound of the formula (1) wherein each of Q$_1$ and Q$_2$ independently represents an alkylene group of 2 to 4 carbon atoms.

6. A process according to claim 5 wherein each of Q$_1$ and Q$_2$ independently represents ethylene or propylene.

7. A process according to claim 1 which comprises the use of a compound of the formula

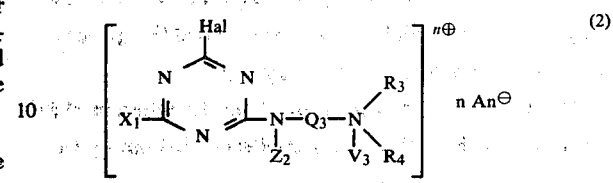

wherein

X$_1$ represents lower alkoxy, —NH$_2$ or the group of the formula

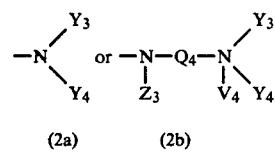

each of Q$_3$ and Q$_4$ independently represents alkylene of 2 to 4 carbon atoms, each of Z$_2$ and Z$_3$ independently represents hydrogen, methyl or ethyl, each of R$_3$, R$_4$, Y$_3$ and Y$_4$ independently represents lower alkyl, and each of V$_3$ and V$_4$ independently represents lower alkyl or benzyl, and Hal, n and An$^\ominus$ have the meanings given in claim 1.

8. A process according to claim 7 which comprises the use of a triazine compound of the formula

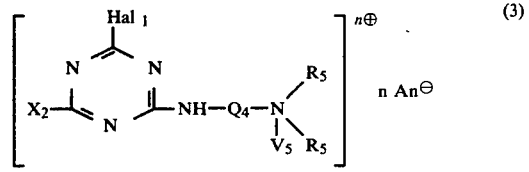

wherein

Hal$_1$ represents fluorine or chlorine,

X$_2$ represents lower alkoxy, —NH$_2$ or the group of the formula

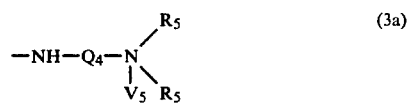

Q$_4$ represents ethylene or propylene,

R$_5$ represents methyl or ethyl,

V$_5$ represents methyl, ethyl or benzyl, and

An$^\ominus$ and n have the meanings given to claim 1.

9. A process according to claim 8 which comprises the use of a triazine compound of the formula (3) wherein X$_2$ represents lower alkoxy and Hal$_1$ represents chlorine.

10. A process according to claim 1 wherein the treatment of the cellulose material with the cationic compound of the formula (1) is carried out by a padding process.

11. A process according to claim 10 wherein the treatment of the cellulose material by a padding process is carried out before, during, or after dyeing.

12. A process according to claim 11 wherein the treatment of the cellulose material by a padding process is carried out before or during dyeing.

13. A process according to claim 10 wherein the treatment of the cellulose material is carried out by the cold padbatch method.

14. A process according to claim 13 wherein the treatment of the cellulose material is carried out by the cold padbatch method during dyeing.

15. A process according to claim 1 wherein the treatment of the cellulose material with the cationic compound of the formula (1) is carried out by the exhaustion process before or during dyeing.

16. An aqueous liquor for carrying out the process according to claim 1, which contains a cationic compound of the formula (1).

17. The cellulose fibre material which is treated according to claim 1.

* * * * *

UNITED STATES PATENT AND TRADEMARK OFFICE
CERTIFICATE OF CORRECTION

PATENT NO. : 4,246,670
DATED : JANUARY 27, 1981
INVENTOR(S) : PIERRE PERRIN ET AL

It is certified that error appears in the above-identified patent and that said Letters Patent are hereby corrected as shown below:

Claim 4, Column 13, line 63, "claim 4" should read

-- claim 3 --.

Signed and Sealed this

Twenty-sixth Day of January 1982

[SEAL]

Attest:

Attesting Officer

GERALD J. MOSSINGHOFF

Commissioner of Patents and Trademarks